(12) United States Patent
Ueno et al.

(10) Patent No.: US 7,943,596 B2
(45) Date of Patent: May 17, 2011

(54) MEDICINAL COMPOSITION FOR OPHTHAL USE CONTAINING ACETYLATED HYALURONIC ACID

(75) Inventors: Norio Ueno, Yokohama (JP); Takashi Oka, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 296 days.

(21) Appl. No.: 12/151,702

(22) Filed: May 8, 2008

(65) Prior Publication Data

US 2008/0221064 A1    Sep. 11, 2008

Related U.S. Application Data

(63) Continuation of application No. 10/545,409, filed as application No. PCT/JP2004/002365 on Feb. 27, 2004, now abandoned.

(30) Foreign Application Priority Data

Feb. 27, 2003   (JP) ................................. 2003-051161

(51) Int. Cl.
*A61K 31/728* (2006.01)
*C07H 5/06* (2006.01)
*C07H 13/04* (2006.01)
*C08B 37/00* (2006.01)

(52) U.S. Cl. .......... 514/54; 514/62; 536/123.1; 536/119

(58) Field of Classification Search ..................... None
See application file for complete search history.

(56) References Cited

U.S. PATENT DOCUMENTS

| | | | | |
|---|---|---|---|---|
| 5,679,657 A * | 10/1997 | Oka et al. | ......................... | 514/54 |
| 6,162,801 A * | 12/2000 | Kita | .............................. | 514/167 |
| 6,673,919 B2 * | 1/2004 | Yui et al. | ....................... | 536/124 |
| 7,019,434 B2 * | 3/2006 | Helmbrecht | .................. | 310/309 |

FOREIGN PATENT DOCUMENTS

| | | |
|---|---|---|
| JP | 60-84225 | 5/1985 |
| JP | 6-9707 | 1/1994 |
| JP | 8-53501 | 2/1996 |
| JP | 9-71602 | 3/1997 |
| JP | 11-236319 | 8/1999 |
| JP | 2001-516713 | 10/2001 |

OTHER PUBLICATIONS

Merriam-Webster's Collegiate Dictionary, published 1998 by Merriam-Webster, incorporated, p. 924.*

Oka, T., et al. "Differential scanning calorimetry studies on the mechanism of skin-softening effect of sodium acetylhyaluronate," Polymer, 2000, pp. 6055-6059, vol. 41, Elsevier Science Ltd.

Oka, T., et al. "Skin-softening effect of acetylhyaluronate on stratum corneum," Journal of Cosmetic Science, May/Jun. 1999, pp. 171-184, vol. 50.

Shimmura et al. British Journal of Ophthalmology (1995), vol. 79, pp. 1007-1077.

* cited by examiner

*Primary Examiner* — Eric S Olson

(74) *Attorney, Agent, or Firm* — Hamre, Schumann, Mueller & Larson, P.C.

(57) ABSTRACT

The present invention provides an ophthalmic pharmaceutical composition containing acetylated hyaluronic acid and a pharmacologically acceptable carrier. Preferably, the average molecular weight of the acetylated hyaluronic acid is 10,000 to 1,000,000, and the acetyl group substitution number is from 2.0 to 4.0. In a preferred embodiment, this ophthalmic pharmaceutical composition is used in the treatment or prevention of dry eye, and in an even more preferred embodiment it is a dry-eye instillation.

3 Claims, No Drawings

MEDICINAL COMPOSITION FOR OPHTHAL USE CONTAINING ACETYLATED HYALURONIC ACID

This application is a Continuation of application Ser. No. 10/545,409, filed Aug. 12, 2005, which is a U.S. National Stage Application of International No. PCT/JP2004/002365, filed Feb. 27, 2004, which applications are incorporated herein by reference.

FIELD OF THE INVENTION

The present invention relates to an ophthalmic pharmaceutical composition that contains acetylated hyaluronic acid and has excellent moisture retention.

BACKGROUND OF ART

The number of patients or pseudo-patients complaining of dry eye (dryness of the eyes) is expected to continue to climb as our society ages and as people increasingly strain their eyes by watching television and using office equipment such as word processors and personal computers. The cause of dry eye is a reduction in lacrimal quantity or a qualitative change in the components thereof, and this disorder can result in scratching or other damage when the surface of the eye becomes dry. Symptoms include eye pain or fatigue, increased blinking, and bloodshot eyes. Further, bacteria may enter through a scratch and cause infection, and if the scratch is deep enough it can even affect the vision of the person. In addition to eyestrain, causes of dry eye include Sjogren's syndrome, Stevens-Johnson syndrome, burns and injury to the eye, and side effects of hypotensive drugs, tranquilizers, eyedrops for treating glaucoma, and other such drugs.

Eyedrops are an effective way to treat dry eye, and dry-eye treatment drugs whose main component is hyaluronic acid are currently attracting much attention and are widely used. Hyaluronic acid is a biologically derived macromolecular substance, has extremely high water retention and characteristic properties such as a high viscoelasticity, a good thickening property, and a good thread-forming, ability, and has been used as a humectant in topical agents for treating various kinds of skin problems and so forth. In the case of dry eye caused by Sjogren's syndrome, in which dryness is seen over' the entire body, the application of eyedrops containing hyaluronic acid is effective all by itself, but when the symptoms are severe, hyaluronic acid-containing eyedrops alone may not provide a sufficient effect, and it is sometimes necessary for the treatment to entail tear duct blockage by means of a tear duct plug. Also, hyaluronic acid has a relatively short residence time on the cornea, so the effect of hyaluronic acid eyedrops lasts only about 2 or 3 hours, which means that the patient must apply the drops more frequently (such as 5 to 10 times a day). There is therefore a need for an ophthalmic pharmaceutical composition that would provide a long-lasting humectant effect, and therefore require fewer applications and improve the QOL (quality of life) of the patient.

Japanese Laid-Open Patent Application S62-68402 discloses a derivative of hyaluronic acid, namely, a hyaluronic acid that has undergone partial esterification of its carboxyl groups, and suggests that this derivative is effective as a drug carrier. However, it has yet to be confirmed that an ophthalmic preparation containing this carboxyl group partially esterified hyaluronic acid derivative as a carrier is effective in pharmaceutical compositions used for dry eye, which must provide a long-lasting humectant effect.

DISCLOSURE OF THE INVENTION

It is an object of the present invention to provide pharmaceutical composition for dry eye, which remains on the cornea and exhibits a humectant effect for a longer period.

The inventors were surprised to learn that when an acetylated derivative of hyaluronic acid is used as an ophthalmic pharmaceutical composition, this derivative stays longer than hyaluronic acid on a soft contact lens, which is a model for the corneal epithelium. Thus, an ophthalmic pharmaceutical composition that contains acetylated hyaluronic acid was found to exhibit a humectant effect over a longer period than an ophthalmic pharmaceutical composition containing just hyaluronic acid.

Therefore, the present invention provides an ophthalmic pharmaceutical composition containing acetylated hyaluronic acid and a pharmacologically acceptable carrier. Preferably, the average molecular weight of the acetylated hyaluronic acid is from 10,000 to 1,000,000, and the acetyl group substitution number is 2.5 to 4.0, even more preferably the average molecular weight of the acetylated hyaluronic acid is approximately 100,000 and the acetyl group substitution number is approximately 3.3. In a preferred aspect, this ophthalmic pharmaceutical composition is used for the treatment or prevention of dry eye, and in an even more preferred aspect, it is a dry-eye instillation.

BEST MODE FOR CARRYING OUT THE INVENTION

When applied to the eye, the acetylated hyaluronic acid-containing ophthalmic pharmaceutical composition pertaining to the present invention exhibits better moisture retention than an ophthalmic pharmaceutical composition containing hyaluronic acid. The corneal epithelium of the eye is composed of about five cell layers, and it some ways is similar to the horny layer of the skin, but the cellular surface of the topmost layer of the cornea is not at all hydrophilic, and in fact is believed to be somewhat hydrophobic. This hydrophobic property can also be predicted from the fact that the lacrimal film has a three-layer structure comprising an oil layer (the uppermost layer), a water layer (the middle layer), and a mucous layer (the lowermost layer) that is contact with the corneal epithelium, and mutin, which is a mucous component made up primarily of polysaccharide, is present in this lowermost layer. Because its hydroxyl groups have been acetylated, acetylated hyaluronic acid is more highly hydrophobic than hyaluronic acid. Therefore, while not particularly bound to theory, the reason that the moisture retention of acetylated hyaluronic acid is better than that of hyaluronic acid, that is, that acetylated hyaluronic acid remains on the cornea longer than hyaluronic acid does, is believed to be that acetylated hyaluronic acid is hydrophobic just like the corneal layer. Also, because it is so highly hydrophilic, there is the danger that hyaluronic acid will absorb moisture from the corneal epithelial tissue. In this regard, acetylated hyaluronic acid is believed to absorb less moisture from the corneal epithelial tissue because it is somewhat less hydrophilic than hyaluronic acid.

The acetylated hyaluronic acid in the present invention is a derivative in which the hydroxyl groups of hyaluronic acid have been acetylated, and more specifically has the following structural formula.

[Chemical Formula 1]

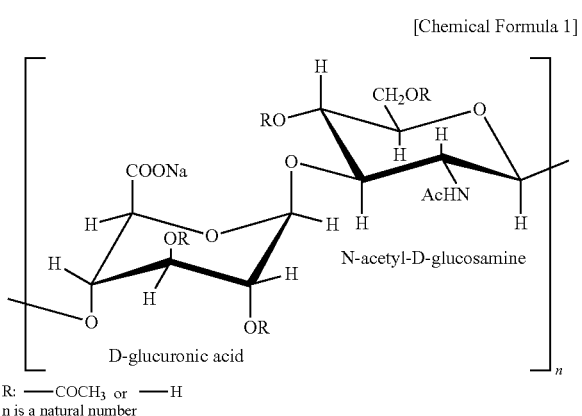

R: —COCH₃ or —H
n is a natural number

Acetylated hyaluronic acid can be manufactured by any method known to persons skilled in the art, and examples of such methods are disclosed in Japanese Laid-Open Patent Application H8-53501.

Preferably, the acetylated hyaluronic acid in the present invention is obtained by suspending powdered hyaluronic acid in an acetic anhydride solvent, and adding concentrated sulfuric acid to bring about acetylation. With this method, an acetylated hyaluronic acid with a high degree of acetylation can be obtained if acetic acid is mixed with the acetic anhydride solvent and the ratio of acetic acid to acetic anhydride is set between 1:4 and 1:1. Also, acetylation will proceed more moderately and the degree of acetylation can be fine tuned if acetic acid is mixed with the acetic anhydride solvent and the ratio of acetic acid to acetic anhydride is set between 2:1 and 4:1. The concentrated sulfuric acid is preferably added to the solvent in an amount of 2 to 7 vol %.

There are no particular restrictions on the acetyl group substitution number of the acetylated hyaluronic acid pertaining to the present invention, but 2.5 to 4.0 is preferable, 2.8 to 3.8 is even better, and 3.0 to 3.8 is better yet. Ideally, the acetyl group substitution number of the acetylated hyaluronic acid pertaining to the present invention is approximately 3.3. It is believed that the humectant effect attributable to hyaluronic acid being inherently hydrophilic will be lost if the acetyl group substitution number is too high, but that the humectant effect attributable to acetylated hyaluronic acid being inherently hydrophobic (which is assumed because the cornea is hydrophobic) will be lost if the acetyl group substitution number is too low. There are four alcoholic hydroxyl groups present in the repeating units of hyaluronic acid, as indicated by Chemical Formula 1 above, and "acetyl group substitution number" refers to how many of these have been substituted with an acetyl group.

The above-mentioned acetylated hyaluronic acid can be refined into high-purity acetylated hyaluronic acid by adding crude acetylated hyaluronic acid to an acetone aqueous solution, adding and dissolving sodium lactate, and adding a high concentration of acetone. The above-mentioned sodium lactate is preferably added in an amount of 1 to 3 wt % with respect to the acetone aqueous solution.

"Hyaluronic acid" as used in the present invention means hyaluronic acid and hyaluronates, and types of various molecular weight can be used. There are no particular restrictions on the average molecular weight of the acetylated hyaluronic acid pertaining to the present invention, but it is preferably 1,000 to 1,000,000, and even more preferably 10,000 to 1,000,000. The ideal average molecular weight is approximately 100,000.

The amount of acetylated hyaluronic acid contained in the ophthalmic pharmaceutical composition of the present invention is 0.01 to 10 weight/volume (weight) %, and preferably 0.05 to 5 weight/volume (weight) %, and even more preferably 0.1 to 1 weight/volume (weight) %, based on the total volume (or total weight) of the pharmaceutical composition. The acetylated hyaluronic acid concentration refers to the weight/volume (w/v) % in the case of a liquid eye wash or eyedrops, and to weight/weight (w/w) % in the case of a solid eye ointment. While it will depend on the hyaluronic acid and its molecular weight, an aqueous solution in which the concentration is over 3% usually cannot be used for eyedrops because its viscosity will be too high, but preparing an aqueous solution of acetylated hyaluronic acid with a concentration of about 10% is quite possible.

The pH of the ophthalmic pharmaceutical composition of the present invention is preferably close to neutral, and is usually from 6.5 to 7.5. The osmotic pressure ratio is preferably adjusted to about 0.5 to 4.0, with a range of 1.0 to 1.5 being even better. Any means commonly employed for ophthalmic pharmaceutical compositions can be used to adjust the pH and osmotic pressure.

The ophthalmic pharmaceutical composition pertaining to the present invention is effective against symptoms of eye dryness, and particularly in the treatment and prevention of dry eye. Dry eye can be caused by a variety of factors, such as eyestrain, Sjogren's syndrome, Stevens-Johnson syndrome, burns and injury to the eye, and side effects of hypotensive drugs, tranquilizers, eyedrops for treating glaucoma, and other such drugs. The ophthalmic pharmaceutical composition of the present invention is formulated as eyedrops, an eye wash, an eye ointment, or the like.

Depending on its formulation, the ophthalmic pharmaceutical composition of the present invention can also be used together with a pharmacologically acceptable carrier. The carrier for eyedrops and eye washes can be any type ordinarily used for such purposes, and purified water is favorable.

The ophthalmic pharmaceutical composition of the present invention may optionally be compounded with various components other than acetylated hyaluronic acid, such as sugars, electrolytes, amino acids, vitamins, lipids, medicinal additives, and medicines. Examples of these components include sugars such as glucose, maltose, etc., oligosaccharides, mannitol, and sugar alcohols such as sorbitol; electrolytes such as sodium chloride, sodium hydrogenphosphate, potassium chloride, magnesium sulfate, and calcium chloride; amino acids such as glycine and alanine; vitamins such as thiamin hydrochloride, sodium riboflavin phosphate, pyridoxine hydrochloride, nicotinic acid amide, folic acid, biotin, vitamin A, L-ascorbic acid, and α-glycosyl ascorbic acid; and derivatives of these. These may be compounded in suitable combinations as needed.

As long as the humectant effect of the present invention is not compromised, it is also possible to add any additives that are used in ordinary ophthalmic preparations, examples of which include preservatives such as methyl parahydroxybenzoate, sodium dehydroacetate, and benzalkonium chloride; stabilizers such as sodium edetate and sodium hydrogensulfite; buffers such as borax, boric acid, and sodium hydrogencarbonate; thickeners such as methyl cellulose, carboxymethyl cellulose, chondroitin sulfuric acid, polyvinyl alcohol, and pullulan; and dissolution improvers such as Polysorbate 80.

If the ophthalmic pharmaceutical composition of the present invention is an ointment, any commonly used and pharmacologically acceptable ointment carrier can be used, specific examples of which include ophthalmic white vaseline and plastibase. Liquid paraffin or the like may also be used as an additive. The ophthalmic pharmaceutical composition of the present invention may additionally contain as needed methylprednisolone and other such steroidal hormones, tetracycline and other such antiphlogistics, penicillin G and other such antibiotics, cyclosporin and other such immunosuppressants, and pharmaceutical products such as immunomodulators, analgesics, autoserum, and hyaluronic acid.

The dosage and method of administration of the ophthalmic pharmaceutical composition of the present invention can be suitably adjusted according to the symptoms of the patient. In the case of an instillation, usually about one to four drops (assuming one drop to be about 0.05 mL) are administered each time, either once or several times daily (such as one to five times, and preferably one to three times). In the case of an eye wash, the patient should use a special eye wash container, a wash bottle, or the like, and wash the eyes from one to several times a day (such as one to five times, and preferably one to three times). In the case of an eye ointment, the inside of the conjunctival sac should be coated with a suitable quantity about one to three times a day.

The use of acetylated hyaluronic acid makes it possible to provide an ophthalmic pharmaceutical composition for dry eye, which remains on the cornea and exhibits a humectant effect over a longer period than when hyaluronic acid is contained.

Examples of the present invention will now be given, but do not limit the scope of the present invention.

EXAMPLES

In their research for the present invention, the inventors examined the ability of acetylated hyaluronic acid (hereinafter referred to as "AcHA") to suppress moisture evaporation, using a soft contact lens (SCL) as a substitute for a human or animal cornea, in an attempt to apply AcHA to an ophthalmic pharmaceutical composition used for the treatment of dry eye.

Experimental Materials and Methodology

The SCLs used as a substitute cornea were Focus Dailies (disposable, 13.8 mm diameter) from Ciba Vision (Tokyo).

The SCLs used in the experiment were made from Nelfilcon A, which is a hydrogel based on a therapeutic material (polyvinyl alcohol, PVA) that has good biocompatibility and is used for surgical sutures and artificial blood vessels. This SCL retains a large amount of water (69%) and has satisfactory oxygen permeability. Accordingly, this SCL has good biocompatibility and good affinity with the cornea, making it suitable as a substitute cornea in physical property research such as this (such as measuring the amount of moisture evaporation).

An isotonic phosphate buffer saline (PBS) (prepared from Dulbecco's PBS (−) powder "Nissui" made by Nissui Pharmaceutical (Tokyo)) was used as a control instillation, while Hyalein 0.1 (containing 0.1 w/v % sodium hyaluronate; average molecular weight of hyaluronic acid: 600,000 to 1,200,000; made by Santen Pharmaceutical (Osaka)) was used as a hyaluronic acid (HA) instillation. The AcHA instillation was prepared by dissolving AcHA (estimated average molecular weight of approximately 100,000; acetylation substitution number of approximately 3.5) in PBS so that the final concentration would be 0.1 w/v %.

The AcHA was prepared as follows.

Twenty milliliter of commercially available special grade acetic acid and 80 mL of acetic anhydride were put in an Erlenmeyer flask with a volume of 300 mL, to which 6 g of a fine powder of hyaluronic acid (average molecular weight of approximately 1200 kd, made by Shiseido) was added a little at a time while stirring. Four milliliter of concentration sulfuric acid was then added slowly, and the system was stirred for 1 hour at room temperature to bring about an acetylation reaction. The reaction solution was in the form of a viscous white liquid.

Two liter of purified water was put into a 3 L glass beaker, and the above-mentioned reaction solution was slowly added in the form of a fine stream while stirring. The precipitate of acetylated hyaluronic acid thus produced was collected and washed twice with 2 L of purified water. This precipitate was then transferred to a 1 L glass beaker, 250 mL of an aqueous 80% (v/v) acetone solution and 9 g of a 50% sodium lactate aqueous solution were added, and the precipitate was completely dissolved under stirring. Four hundred milliliter of acetone was then added slowly, and a gel of acetylated hyaluronic acid was reprecipitated. This precipitate was collected, after which it was washed twice for 10 minutes each time in a homogenizer at a speed of 10,000 rpm and using 100 mL of ethanol. The precipitate was then collected by reduced pressure filtration, after which it was dried under reduced pressure, which gave a white powder of acetylated hyaluronic acid.

Measurement Method

An AG64 balance made by Mettler Toledo was used to weigh the SCL, and weight data were sent to and stored in a personal computer. Nonparametric testing, which is not affected by the distribution of data, was employed for the statistical analysis of the data.

The experiments (the application of the eyedrops on SCLs, leaving them in the eyes, and measuring the weight of SCLs) were conducted in a thermohygrostatic room at a temperature of 25° C. and a humidity of 50%. Each SCL packaged in a isotonic phosphate buffer was taken out with dental forceps and placed convex-side up on the pre-weighed lid (30 mm diameter) of a plastic petri dish, the weight of the petri dish including the SCL was measured, and 20 μL of sample instillation was immediately dropped onto the center of the SCL. After 20 minutes had elapsed, the weight of the petri dish including the SCL was measured, and another 20 μL of sample instillation was immediately dropped onto the center of the SCL. This cycle of measurement and sample dropping was repeated a total of four times at 20 minute intervals. After the final sample dropping, the SCL was weighed every 20 minutes until 120 minutes after the start of the experiment.

Experiment Results

As shown in Table 1 below, the SCLs in the AcHA instillation group at 120 minutes after the start of the experiment had significantly lower moisture evaporation amounts than the control instillation group or the HA instillation group.

TABLE 1

| Relative wet weight (%) of soft contact lens after several instillations | | | |
|---|---|---|---|
| Time (min) | Control instillation | HA instillation | AcHA instillation |
| 80 | 130.4 | 145.2*$^a$ | 149.2*$^b$ |
| 100 | 105.1 | 118.1*$^a$ | 123.9*$^b$ |
| 120 | 82.13 | 86.03 | 99.8*$^{b,}$*$^c$ |

*$^a$with respect to the control instillation group; p < 0.05)
*$^b$with respect to the control instillation group; p < 0.05)
*$^c$with respect to the HA instillation group; p < 0.05)

The numerical values are the median value for each group, and the number of observations was 5 for the control instillation group and HA instillation group, and 4 for the AcHA instillation group. The Mann-Whitney method (a nonparametric test) was used for a significant different test.

CONCLUSION

The evaporation of moisture from an SCL was significantly suppressed with a 0.1% AcHA instillation. It is clear from this that the AcHA instillation has the potential for application as an instillation in the treatment of dry eye.

| AcHA instillation composition | |
|---|---|
| acetylated hyaluronic acid | 0.1 g |
| benzalkonium chloride | 0.002 g |
| isotonic phosphate buffer | q.s. |
| total | 100 mL |

With the above composition, AcHA can be contained in an amount of about 0.1 to 10 g, and since AcHA has a high molecular weight (approximately 100,000), even at a high concentration it will be unlikely to have an effect on the osmotic pressure ratio of the instillation.

What is claimed is:

1. A method of treating dry eye, comprising administering to an eye of a subject in need thereof an ophthalmic composition comprising:
    an effective amount of acetylated hyaluronic acid, characterized by chemical formula 1, Chemical Formula 1

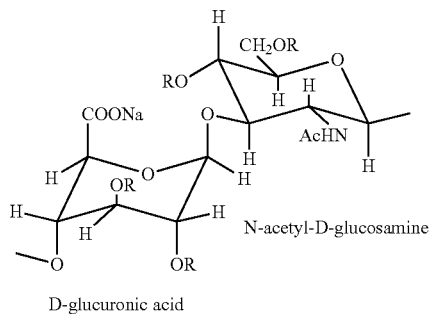

wherein an average molecular weight of the acetylated hyaluronic acid is in a range of 10,000 to 1,000,000, and
at least two of four alcoholic hydroxyl groups in the acetylated hyaluronic acid (—OR) are substituted with an acetyl group; and
a pharmacologically acceptable carrier.

2. The method of claim 1, wherein the composition is in a liquid form and comprises 0.01 to 10 w/v % of the acetylated hyaluronic acid.

3. The method of claim 1, wherein the composition is in an ointment form and comprises 0.01 to 10 w/w % of the acetylated hyaluronic acid.

* * * * *